(12) United States Patent
Fleming et al.

(10) Patent No.: US 8,343,148 B2
(45) Date of Patent: Jan. 1, 2013

(54) SURGICAL INSTRUMENT

(75) Inventors: Alistair I. Fleming, Cambridge (GB);
Julian M. Ebbutt, Cardiff (GB);
Andrew E. Jenkins, Glamorgan (GB);
Hollie Johnston, Wiltshire (GB);
Rhodri G. James, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 565 days.

(21) Appl. No.: 12/453,008

(22) Filed: Apr. 27, 2009

(65) Prior Publication Data

US 2009/0292281 A1 Nov. 26, 2009

Related U.S. Application Data

(60) Provisional application No. 61/129,272, filed on Jun. 16, 2008.

(30) Foreign Application Priority Data

May 20, 2008 (GB) .................................. 0809160.5

(51) Int. Cl.
*A61B 18/18* (2006.01)
(52) U.S. Cl. ........................................... 606/48; 606/45
(58) Field of Classification Search ............... 606/46–51
See application file for complete search history.

(56) References Cited

U.S. PATENT DOCUMENTS

| | | | | |
|---|---|---|---|---|
| 5,810,806 A | * | 9/1998 | Ritchart et al. | 606/45 |
| 5,957,884 A | * | 9/1999 | Hooven | 604/48 |
| 6,749,560 B1 | | 6/2004 | Konstorum et al. | |
| 2002/0058859 A1 | | 5/2002 | Brommersma | |
| 2002/0193792 A1 | | 12/2002 | Valencic et al. | |
| 2003/0139741 A1 | * | 7/2003 | Goble et al. | 606/48 |
| 2007/0225562 A1 | | 9/2007 | Spivey et al. | |

FOREIGN PATENT DOCUMENTS

GB    2 214 428 A    9/1989

(Continued)

OTHER PUBLICATIONS

Search Report in International Application No. PCT/GB2008/004065, mailed Feb. 23, 2009.
Search Report, dated Sep. 16, 2008, in corresponding U.K. Application No. 0809160.5, filed May 20, 2008.
Search Report in International Application No. PCT/GB2009/001199, mailed Jun. 29, 2009.
International Preliminary Report on Patentability in International Application No. PCT/GB2009/001199, completed May 7, 2010.

*Primary Examiner* — Nicholas Lucchesi
*Assistant Examiner* — Rebecca E Eisenberg
(74) *Attorney, Agent, or Firm* — Nixon & Vanderhye PC

(57) ABSTRACT

A device for morcellating tissue within a body cavity of a patient comprises a stationary tube having a distal end portion, and a bipolar electrosurgical electrode assembly located at the distal end of the tube. The electrosurgical electrode assembly comprises first and second electrodes separated by an insulation member. When an electrosurgical cutting voltage is applied to the electrode assembly, and relative movement is initiated between the tube and the tissue, a core of severed tissue is formed within the tube such that it can be removed from the body cavity of the patient. The tube comprises a twin-walled construction with an inner wall, an outer wall and an air gap therebetween. This twin-walled construction reduces the heat that is able to travel proximally along the tube.

24 Claims, 5 Drawing Sheets

FOREIGN PATENT DOCUMENTS

| | | |
|---|---|---|
| GB | 2 436 065 | 9/2007 |
| WO | WO 92/10969 | 7/1992 |
| WO | WO 96/24296 | 8/1996 |
| WO | WO 99/62414 | 12/1999 |
| WO | WO 01/24720 | 4/2001 |
| WO | WO 02/062247 | 8/2002 |
| WO | WO 03/057020 A1 | 7/2003 |
| WO | WO 2004/096015 A2 | 11/2004 |
| WO | WO 2005/112806 | 12/2005 |
| WO | WO 2005/120627 A2 | 12/2005 |

* cited by examiner

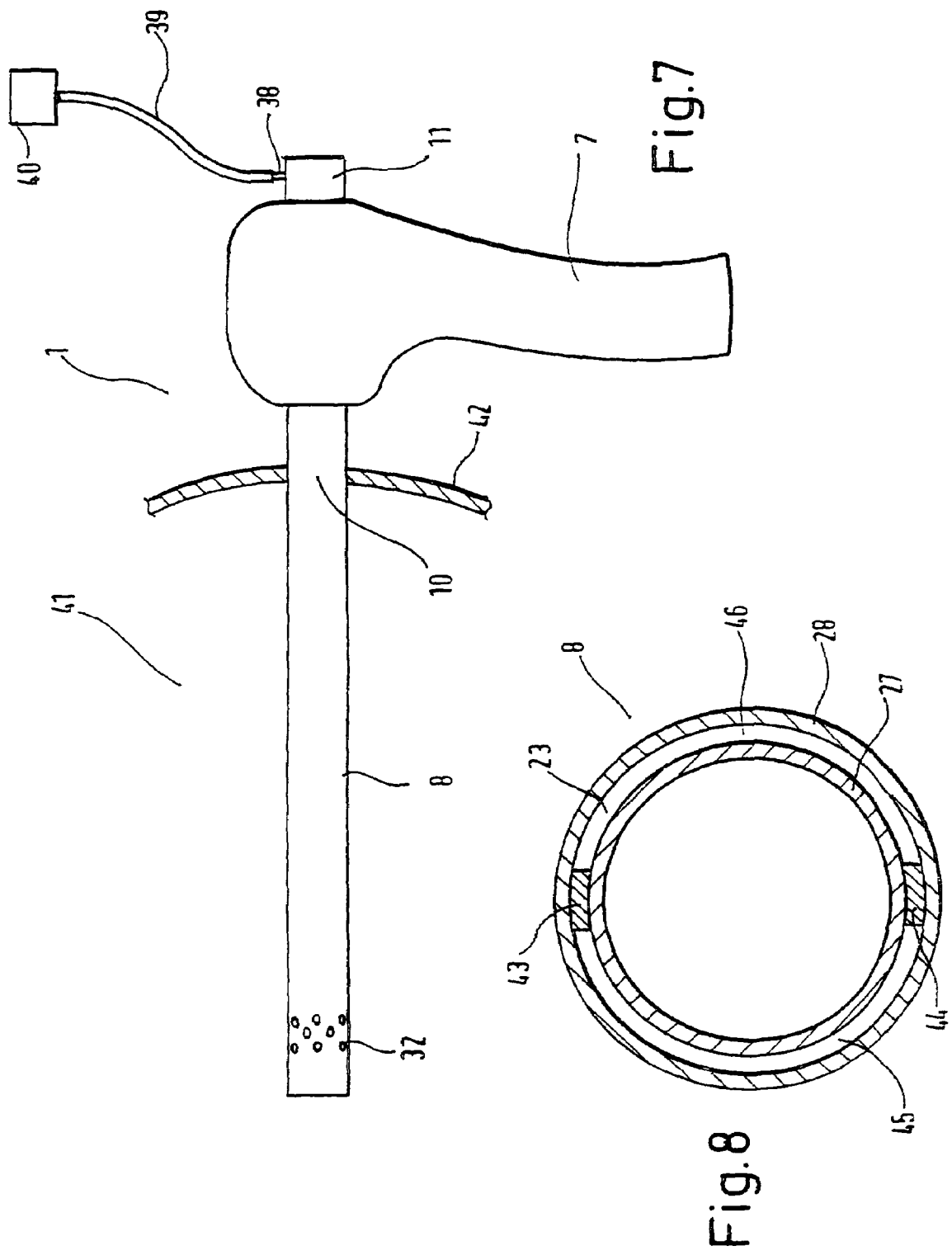

SURGICAL INSTRUMENT

CROSS-REFERENCE TO RELATED APPLICATION

This application claims the benefit of Provisional Application No. 61/129,272, filed 16 Jun. 2008, the entire contents of which are hereby incorporated by reference in the application.

FIELD OF THE INVENTION

This invention relates to a bipolar electrosurgical instrument for use in the bulk removal of tissue, as in a laparoscopic hysterectomy.

BACKGROUND OF THE INVENTION

Our published application WO2005/112806 describes a morcellator, typically used in laparoscopic hysterectomy, in which the body of the uterus is resected from the stump or fundus, and is then removed from the operative site. To enable the uterus to be removed through a limited surgical opening, it is desirable to morcellate it into smaller pieces of tissue, which are easier to remove. The present invention relates to an improvement to this type of instrument.

SUMMARY OF THE INVENTION

Accordingly, there is provided a device for morcellating tissue within a body cavity of a patient, the device comprising a stationary shaft in the form of a tube having a proximal end portion and a distal end portion, the tube having a bipolar electrosurgical electrode assembly located at the distal end portion thereof, the bipolar electrosurgical electrode assembly comprising first and second electrodes separated by an insulation member, the bipolar electrosurgical electrode assembly extending at least partly around the circumference of the distal end portion of the tube, wherein at least the majority of the shaft length is constituted by a twin-walled construction.

Prior art published application WO92/10969 discloses a visualisation device with a twin-walled construction. The twin-walled construction in WO92/10969 allows for fluid to be squeezed through the gap between the twin walls, and "puffed" out of the end of the tube in order to clear the view obtained from looking through the tube. Another prior art document GB 2214428 discloses another tubular surgical device with a twin-walled construction, allowing the device to be anchored to a tissue structure by the application of suction through the gap between the walls.

However, these devices are not morcellators, and they do not have an electrosurgical electrode assembly at the end of the tube. The twin-walled construction of the present invention is provided for an entirely different purpose, namely to control the heat being conducted back along the shaft of the instrument. The electrosurgical electrode assembly at the tip of the device generates a considerable amount of heat; and, if this is allowed to be transferred back up the shaft, the shaft can get undesirably hot. The twin-walled construction reduces the heat transferred to the shaft from the electrosurgical assembly, and prevents the shaft from becoming unacceptably hot. This problem simply does not occur with the two prior art devices described above, as there is no electrosurgical assembly, and no heat generated by the instruments concerned.

In the electrosurgical morcellating device of the present invention, the tube is inserted into the body of a patient such that the proximal end portion of the tube extends from the body, and the distal end portion is within the body. This means that the proximal end portion of the tube passes through the abdominal wall of the patient, sometimes using a port or trocar, but often used without a port or trocar such that the tube is in direct contact with the abdominal wall. In operation of the morcellating device as described in our earlier application WO2005/112806, a slug of tissue is pulled through the tube, having been severed by the electrosurgical cutting assembly at the distal end portion, of the tube. Heat is generated by the electrosurgical cutting of the tissue, and the slug of tissue can retain a considerable amount of heat as it is pulled back through the tube. The twin-walled construction means that, even if the inner wall is in contact with this hot slug of tissue, less heat is transferred to the outer wall due to the disconnect between the inner and outer walls. As it is this outer wall that is likely to be in contact with the patient's skin or other tissue, it is the temperature of the outer wall that is critical to ensuring that there is no unwanted tissue damage caused by the shaft of the instrument. Accordingly, the twin-walled construction preferably extends along the tube from the proximal end portion to the distal end portion. The twin-walled construction keeps the temperature of the outer wall to within reasonable limits ensuring that collateral tissue damage does not occur.

The twin-walled construction preferably extends substantially to the distal end of the tube. This ensures that heat is conducted poorly from the distal end of the tube (where the electrosurgical cutting assembly is located) back along the shaft towards the proximal end of the instrument. Where the instrument is inserted into the body of a patient without a separate port or trocar, the shaft of the instrument will be in direct contact with the abdominal wall of the patient. Any overheating of the shaft of the instrument could therefore result in damage to the abdominal wall, and this is avoided by the twin-walled construction of the present invention.

Additionally, some proximal part of the tube is held by the user of the instrument, or is integrally attached to a handle mechanism which is held accordingly. Excessive heat to the proximal part of the instrument must be avoided, so as to prevent the operation of the instrument becoming uncomfortable for the user. Conveniently, the twin-walled construction abuts the second electrode, so that the inhibiting of heat transfer begins substantially at the electrosurgical assembly.

In one arrangement, the device further comprises a heat-sink member in contact with both the second electrode and the distal end portion of the twin-walled construction. Heat is generated when the electrosurgical assembly is used, and without the heat-sink member, the tip of the instrument could remain unacceptably hot, even after the electrosurgical assembly has been deactivated. The heat-sink member acts to conduct away the heat generated at the tip of the instrument when the electrosurgical assembly is activated. This means that the tip of the instrument does not remain hot enough to cause unwanted tissue damage after the electrosurgical assembly has been deactivated. In one arrangement, the heat-sink member is a relatively large mass of conducting material in contact with, or integral with, the second electrode. By making the twin-walled construction in contact with this heat-sink member, the heat is transferred away from the electrosurgical assembly but not transferred further along the shaft causing the problems previously outlined.

One or both of the walls of the twin-walled construction are typically formed from a polymer material, such as a braided polymer material. This allows the walls to be relatively thin, typically less than 0.5 mm. In one convenient arrangement, the thickness of the walls of the twin-walled construction is substantially 0.2 mm.

By "twin-walled construction" is herein meant to include any construction having two or more walls. The walls may be of the same material or formed from different materials, and may be adjacent one another in the form of a layered or laminated wall, or spaced from one another to provide a gap therebetween.

Conveniently, the twin-walled construction comprises first and second walls with a gap therebetween. Typically, the gap between the walls of the twin-walled construction is an air gap, as air is a sufficiently poor conductor of heat. The gap between the walls of the twin-walled construction is conveniently less than 1 mm, and preferably less than 0.5 mm.

Preferably, at least one of the walls of the twin-walled construction includes an entrance to allow material to enter the gap between the walls, and an exit at a different axial position along the shaft to allow material to exit the gap between the walls. The entrance may be located at the distal end portion of the tube, and the exit may be located at the proximal end portion of the tube, such that the gap between the walls is capable of being used for the extraction of smoke.

Alternatively, the gap between the walls is provided with dividing means, such that it constitutes at least two passages, a first passage having an entrance located at the distal end portion of the tube, and an exit located at the proximal end portion of the tube, such that the first passage is capable of being used for the extraction of smoke, and a second passage having an entrance located at the proximal end portion of the tube, and an exit located at the distal end portion of the tube, such that the second passage is capable of being used for the supply of insufflation fluid. In this way, the gap between the walls can be used for both smoke extraction and insufflation simultaneously. Conceivably, the dividing means comprises one or more internal walls dividing the gap into first and second passages.

Where the gap between the walls of the twin-walled construction is not used for smoke extraction or insufflation, the twin-walled construction conceivably constitutes a closed system and there is a vacuum between the walls of the twin-walled construction. The vacuum helps to inhibit the transfer of heat between the inner and outer walls. Alternatively, the gap between the walls contains an inert gas, such as argon or carbon dioxide, or any other inert gas with poor heat transfer characteristics. Finally, the gap between the walls could conceivably contain a solid material, such as a heat-insulating foam or other poorly conducting material. Such alternatives will be envisaged by those skilled in the art without departing from the scope of the present invention.

The device of the present invention is preferably operated in combination with a tissue-pulling device locatable within the tube and capable of pulling tissue against the distal end of the tube. The use of the tissue-pulling device means that the shaft of the instrument can be maintained stationary with tissue being pulled into the tube, as opposed to the tube being advanced into tissue. This provides greater control for the user of the morcellator instrument.

BRIEF DESCRIPTION OF THE DRAWINGS

The invention will now be described in more detail, by way of example, with reference to the drawings, in which:

FIG. 7 is a schematic view of a further morcellating system constructed in accordance with the invention; and FIG. 8 is a cross-sectional view of an alternative construction to that of FIG. 7.

DESCRIPTION OF PREFERRED EMBODIMENTS

Figure 1:
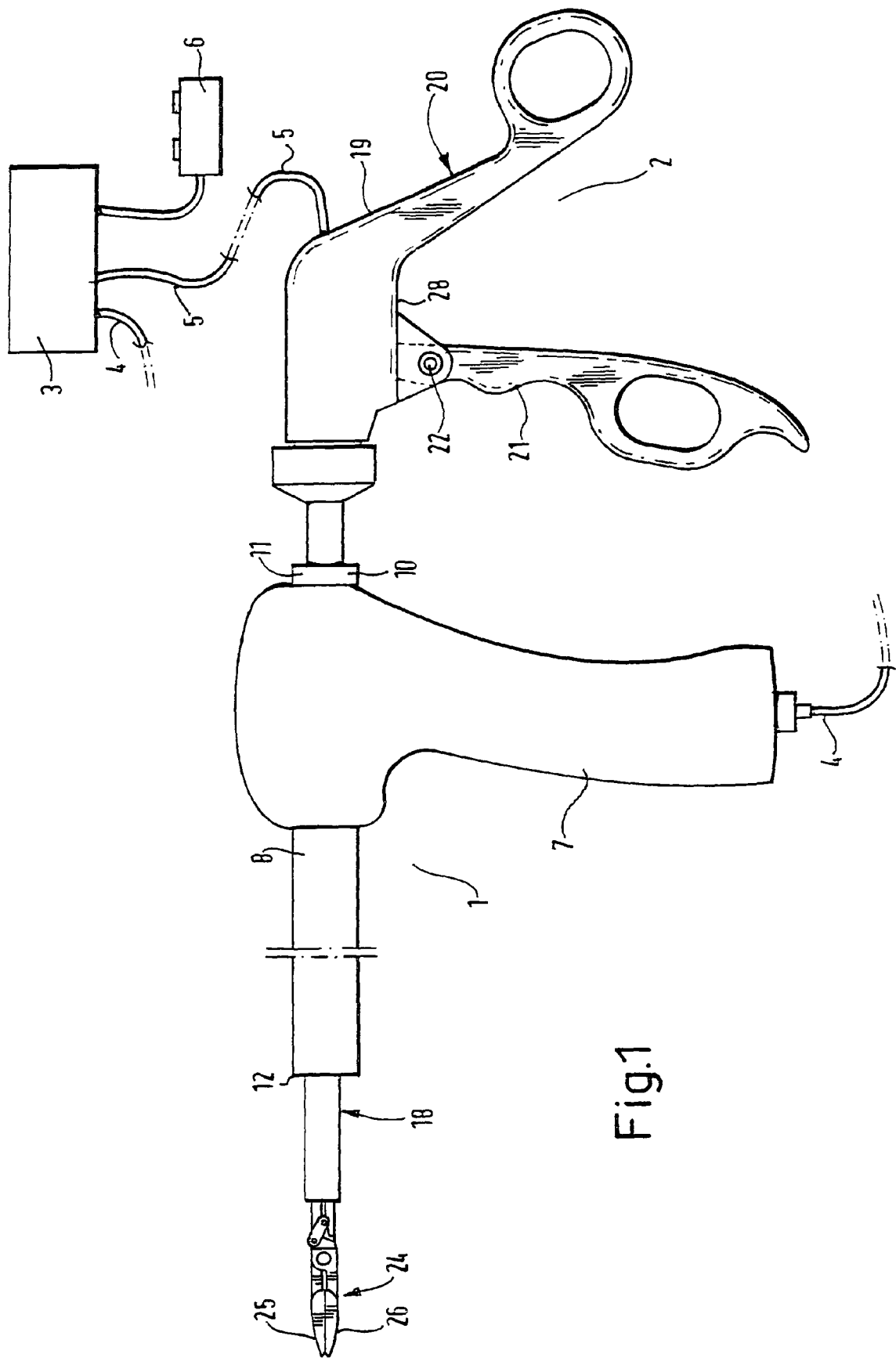
FIG. 1 is a schematic side view, partly in section, of a morcellating system constructed in accordance with the present invention.

Referring to FIG. 1, a morcellating system comprises a morcellating device shown generally at 1, a tissue-pulling device shown generally at 2, and an electrosurgical generator 3. The generator 3 is connected to the morcellating device 1 by means of a cable 4, and to the tissue-pulling device 2 by means of a cable 5. The generator 3 is controlled by means of a footswitch 6.

Figure 2:
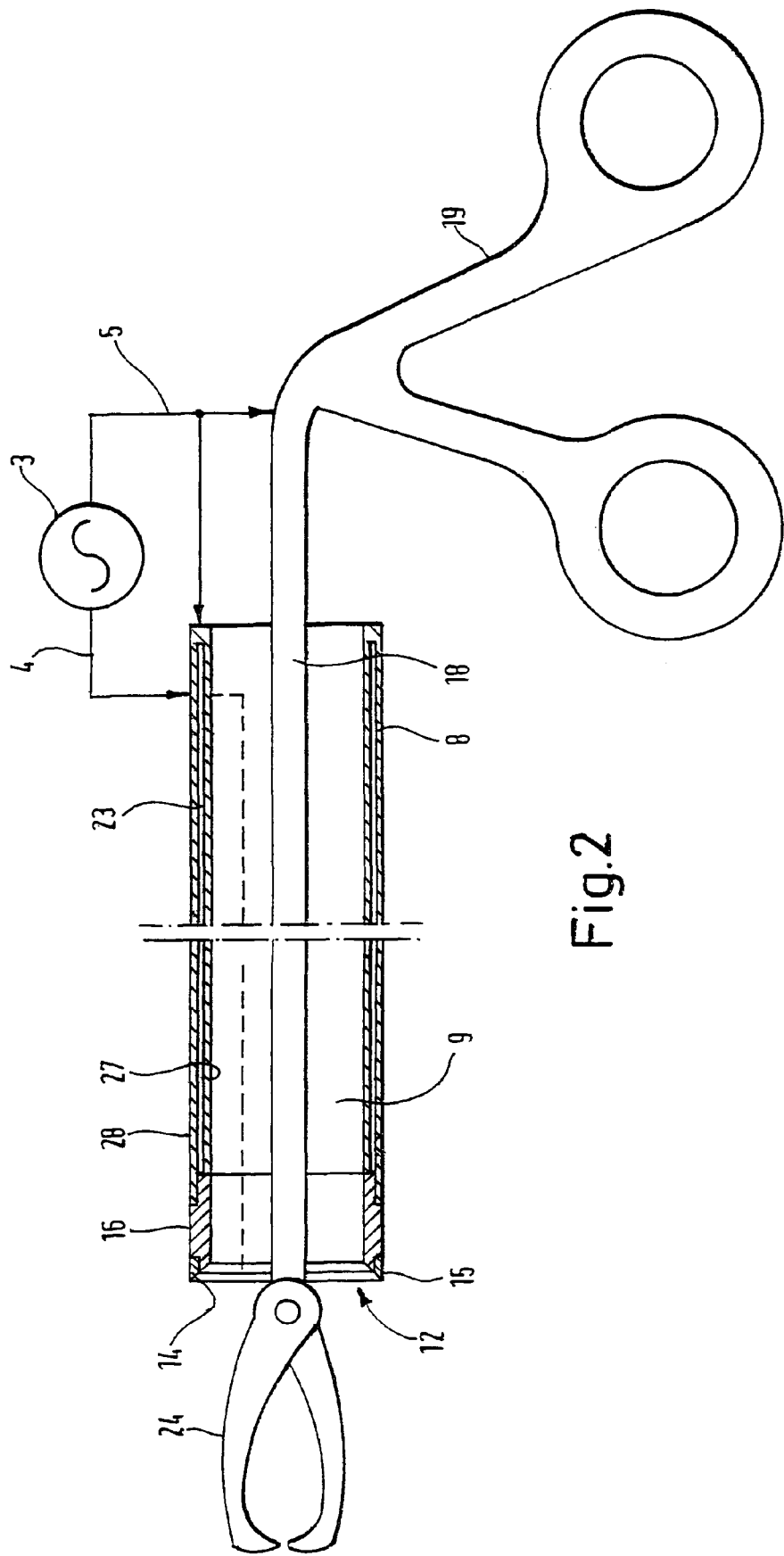
FIG. 2 is a schematic sectional view of a part of the system of FIG. 1.

The morcellating device 1 comprises a handle 7 and a twin-walled cylindrical tube 8. As shown in FIGS. 1 and 2, the cylindrical tube 8 is hollow, and defines a lumen 9 therein. The proximal end 10 of the tube 8 extends from the handle 7 as shown at 11, and the distal end 12 of the tube is provided with an electrosurgical electrode assembly 13. The electrosurgical electrode assembly 13 comprises an active tissue-cutting electrode 14, protruding from an insulation member 15, extending around the circumference of the tube 8. The insulation member 15 separates the electrode 14 from a return electrode 16, which in turn is connected to the twin-walled tube 8.

The return electrode 16 is connected to one pole of the generator 3, while the active electrode 14 is connected to the other pole of the generator, each via the cable 4. In this way, the electrodes 14 and 16 constitute a bipolar electrode assembly, which, when energised by the generator 3, is capable of cutting tissue coming into contact with the distal end of the tube 8.

The tissue-pulling device 2 comprises a tubular shaft 18, at the proximal end of which is a scissors-type handle mechanism 19, having a first handle 20 and a second handle 21. The second handle 21 is pivotable with respect to the first handle 20, about a pivot pin 22.

Pivoting of the second handle 21 causes the opening and closing of a jaw assembly 24 at the distal end of the shaft 18. The jaw assembly 24 comprises a first jaw member 25 and a second jaw member 26, movable between open and closed positions by the movement of the handle 21. The tissue-pulling device 2 is manually translatable in a longitudinal manner within the lumen 9 of the morcellating device 1. The jaw members 25 and 26 are electrically connected to the shaft 18, and the shaft is electrically connected, via the lead 5, to the generator 3. The shaft 18 is connected to the same pole of the generator 3 as the return electrode 16, so that the tissue-pulling device 2 acts as an additional return electrode.

Figure 3:
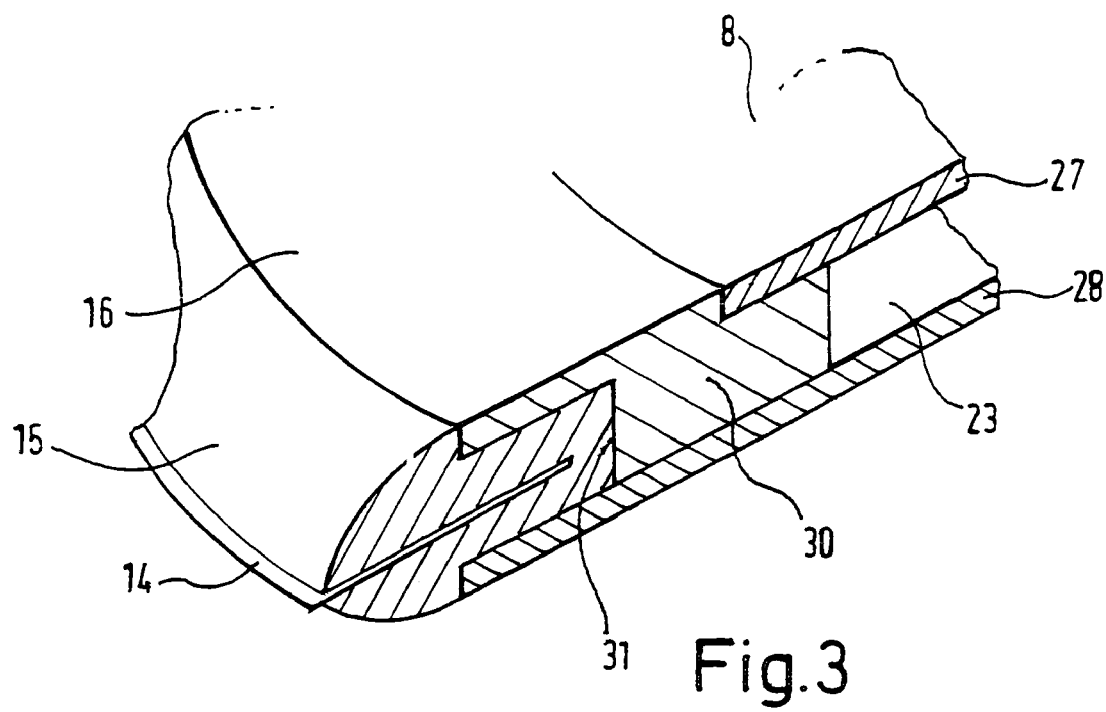
FIG. 3 is an enlarged view of a part of the system of FIG. 2.

The twin-walled construction of the tube 8 is shown in FIG. 2, and in more detail in FIG. 3 which is an enlarged view of the distal end of one wall of the tube. The tube 8 includes an inner wall 27 and an outer wall 28, with an air gap 23 therebetween. The return electrode 16 is provided with an annular heat-sink portion 30, and this heat-sink portion is located between the inner and outer walls 27 and 28. The insulation member 15 is located in a recess 31 formed between the return electrode 16 and the inner wall 27. Finally, the active electrode 14 is embedded in the insulation member 15, such that it projects from the distal end of the tube 8.

The operation of the morcellating system is as follows. The tube 8 of the morcellating device 1 is inserted into the body of a patient, typically without the use of a port or trocar, and is brought into position adjacent to the tissue to be removed (typically a resected uterus in the case of a laparoscopic hysterectomy). The tissue-pulling device 2 is then inserted through the lumen 9 of the morcellating device 1. The handle 21 is operated to open the jaw assembly 24, and the tissue-pulling device 2 is manoeuvred so that tissue from the uterus is located between the jaw members 25 and 26. The handle 21 is then operated to close the jaw assembly 24, grasping tissue therein.

The surgeon operates the footswitch 6 to operate the generator 3 so that an electrosurgical cutting voltage is supplied between the tissue-cutting electrode 14 and the return electrode 16. As mentioned previously, the tissue-pulling device 2 is also electrically connected to the same pole of the generator 3 as the return electrode 16, so that the tissue-pulling member constitutes an additional return electrode. With tissue firmly grasped in the jaw assembly 24, the device 2 is slowly withdrawn from the tube 8, pulling the tissue against the distal end of the tube and the active electrode 14. As the tissue contacts the active electrode 14, it is vaporised, allowing the device 2 to be withdrawn further into the tube 8. In this way, a cylindrical core of tissue is formed in the tube 8, the tissue being withdrawn though the proximal end 10 of the morcellating device 1 (which remains outside the body of the patient) for disposal.

The tissue-pulling device 2 can then be re-inserted into the tube 8 so that a further core of tissue can be removed from the body of the patient. By repeating this process, large quantities of tissue can be removed from the patient in a relatively short time, such that the entire uterus can be removed, if necessary, while still employing a laparoscopic approach.

The twin-walled construction with the air gap 23 ensures that heat generated at the active electrode 14 does not easily pass along the tube 8 towards the handle 7 (not shown in FIG. 2). Heat from the active electrode 14 passing across the insulation member 15 reaches the heat-sink portion 30 of the return electrode 16. This ensures that the active electrode 14 does not remain excessively hot once the electrosurgical cutting voltage is switched off. However, heat is discouraged from passing proximally further along the tube 8 by its twin-walled construction. In addition, if a piece of hot tissue contacts the inner wall 27 during its passage along the tube 8, the air gap 23 will prevent the heat from being transferred to the outer wall 28. As it is the outer wall 28 of the tube that is often in contact with the abdominal wall of the patient or other tissue adjacent to the surgical site, the reduction in heat to this outer wall 28 is most important. By keeping the outer wall 28 relatively cool, the risk of inadvertent damage to the surrounding tissue is minimised.

Figure 4:
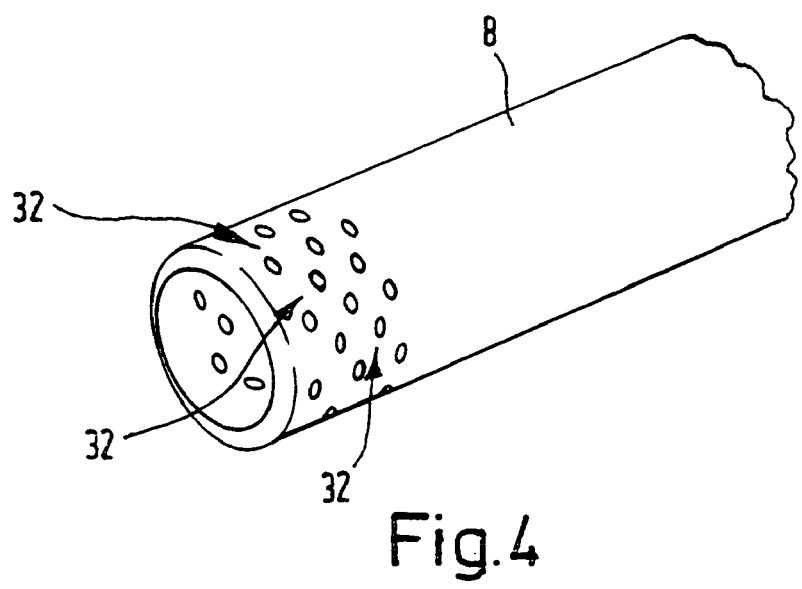
FIG. 4 is a perspective view of an alternative embodiment of morcellating system constructed in accordance with the invention.

The action of the active electrode 14 on the tissue to be morcellated does produce a certain amount of smoke and other debris that can obscure the vision of the surgeon. FIG. 4 shows an alternative embodiment of instrument in which apertures 32 are provided in the outer wall 28, near the distal end of the tube 8. These apertures 32 provide a pathway between the surgical site and the air gap 23 between the inner and outer walls 27 and 28. By applying suction to the air gap 23 at the proximal end of the instrument, smoke can be drawn into the air gap and evacuated away from the surgical site. A corresponding exit (not shown) is provided for the smoke to exit at the proximal end 10 of the tube 8.

Figure 5:
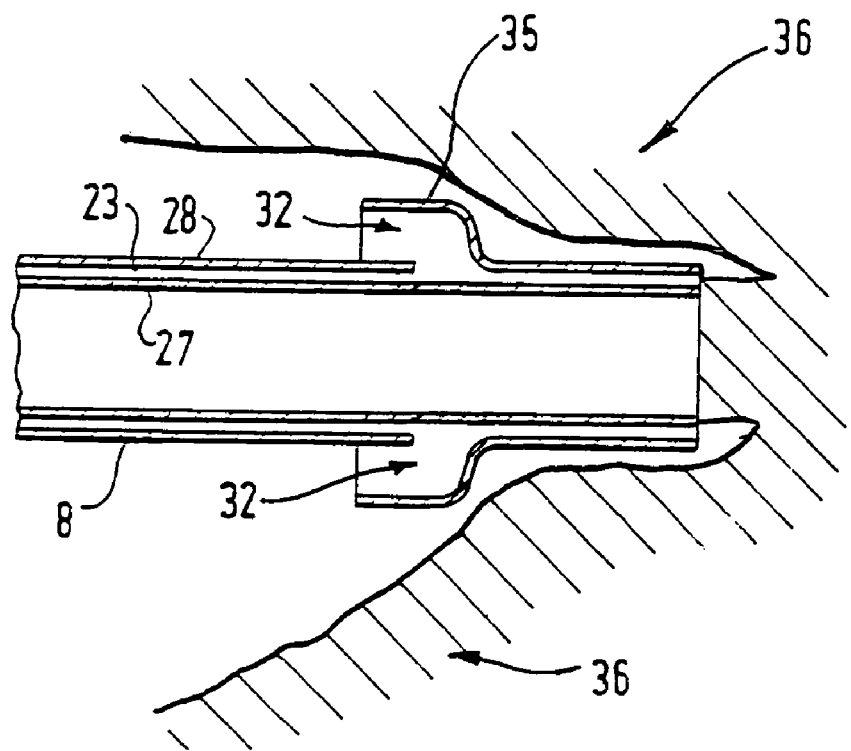
FIG. 5 is a schematic side view of an alternative construction to that of FIG. 4.
Figure 6:
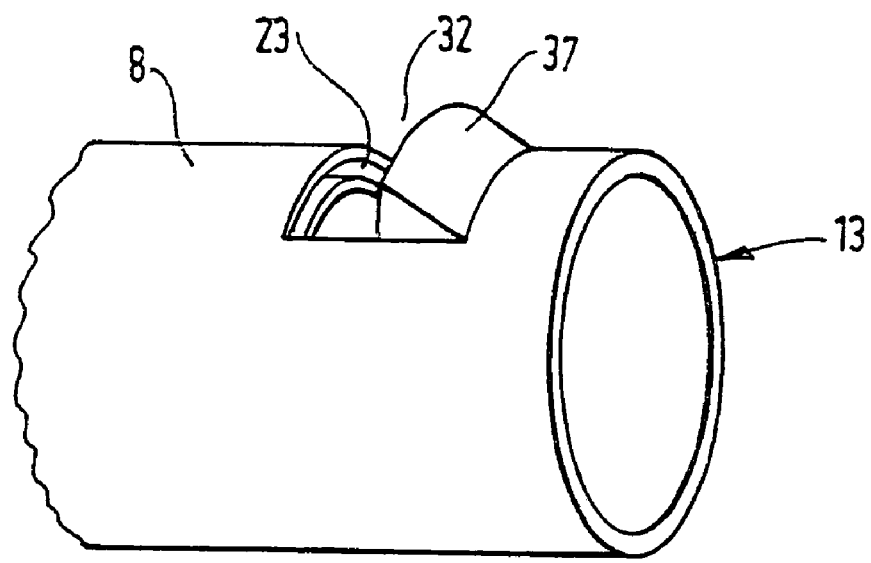
FIG. 6 is a perspective view of a further alternative construction to that of FIG. 4.

FIGS. 5 and 6 show alternative embodiments in which a shield is provided to prevent oversized pieces of tissue from entering the apertures 32. In FIG. 5, the shield is in the form of a flange 35 extending out from the tube 8, and partially covering the apertures 32. This helps to prevent pieces of tissue from entering the apertures 32 and being drawn into the gap 23 between the inner and outer walls (27, 28). The flange 35 also ensures that unsevered tissue 36 adjacent to the apertures 32 is not drawn against the apertures by the action of the suction, thereby blocking them. FIG. 6 shows an alternative embodiment in which the shield is in the form of an upstanding lip 37. This construction allows more effective smoke evacuation, but does not provide as much of a shielding effect as compared with the flange 35 illustrated in FIG. 5.

FIG. 7 shows the morcellating device 1 with the tube 8, the handle 7, and the apertures 32 leading into the gap 23 between the walls (27, 28) of the twin-walled structure of the tube. The other elements such as the electrodes 14, 16 and the generator 3 are present as before, but have been omitted from FIG. 7 for clarity. The distal end of the tube 11 extends from the handle 7, and is provided with a connector 38 to which a hose 39 is connected. The connector 38 provides a communication pathway into the gap 23 between the inner and outer walls 27, 28 at the proximal end 10 of the tube 8, while the apertures 32 provide a communication pathway into the gap between the inner and outer walls at the distal end 12 of the tube. In the arrangement shown in FIG. 7, the hose 39 is connected to an insufflation supply 40, such that the connector 38 constitutes an entrance for insufflation fluid to enter the gap 23 between the walls 27, 28. Consequently, the apertures 32 at the distal end portion 12 of the tube 8 constitute an exit for the insufflation fluid. In this way, the peritoneal cavity 41 can be expanded with an insufflation fluid such as carbon dioxide, using the gap 23 between the walls 27, 28 of the tube to carry the fluid. This means that an additional supply tube, requiring an additional puncture of the abdominal wall 42, is not required.

In the instrument of FIG. 7, if the device 1 starts to create smoke within the peritoneal cavity 41, the insufflation supply can be disconnected and replaced with a vacuum source, such that the apertures 32 constitute an entrance for smoke into the gap 23 between the walls 27, 28 of the tube 8, and the connector 38 constitutes an exit for the smoke on the outside of the abdominal wall 42. However, it may be unsatisfactory to switch continually between insufflation and vacuum, and so the arrangement of FIG. 8 provides a tube 8 in which simultaneous insufflation and smoke extraction can be used. The tube 8 has an inner wall 27 and an outer wall 28 providing a gap 23 therebetween, just as previously described. However, the gap 23 is provided with a first-longitudinally-extending internal wall 43, and a second longitudinally-extending internal wall 44. The internal walls 43 and 44 divide the gap 23 into a first passageway 45 and a second passageway 46, each passageway being separate from the other. In this way, the first passageway 45 can be used for smoke extraction, and the second passageway 46 used for insufflation. As each passageway 45, 46 requires its own entrance and exit, some of the apertures 32 are associated with the first passageway, and other apertures 32 associated with the second passageway. Similarly, at the proximal end 10 of the tube 8, first and second connectors (not shown) are provided, one associated with the first passageway 45 (for connection to a vacuum source) and a second connector associated with the second passageway 46 (for connection to the insufflation supply 40).

Thus, simultaneous smoke extraction and insufflation can be provided, using the twin-walled structure and the divided gap 23 therebetween.

Although these embodiments use the twin-walled construction to provide secondary advantages such as smoke extraction and/or insufflation, the primary advantage associated with the twin-walled construction is its ability to inhibit the transfer of heat to the proximal end portion 10 which may be in contact with the abdominal wall 42. The separation between the inner and outer walls 27, 28, and the poor heat transfer properties of the air gap between the walls, means that heat generated in the inner wall 27 is not easily transferred to the outer wall 28. Thus the outer wall 28 remains relatively cool, ensuring that the abdominal wall or other tissue in contact with the outer wall of the tube 8 is not damaged.

Those skilled in the art will appreciate that other changes to the described devices can be made without departing from the scope of the present invention. For example, in addition to the tissue-pulling device 2 described above, other means for pulling tissue into the tube 8 can be envisaged. The bipolar electrosurgical assembly 13 will be capable of cutting tissue pulled into contact therewith, by any suitable means. Other alternatives include those for the twin-walled construction, including multilayered laminate structures, providing a vacuum between the walls, or filing the gap with different materials such as foam or an inert gas. Such alternatives will be envisaged by those skilled in the art without departing from the scope of the present invention.

What is claimed is:

1. A device for morcellating tissue within a body cavity of a patient, the device comprising:
a stationary shaft in the form of a tube having a proximal end portion and a distal end portion, the tube having a stationary bipolar electrosurgical electrode assembly located at the distal end portion thereof, the bipolar electrosurgical electrode assembly comprising first and second electrodes separated by an insulation member, the bipolar electrosurgical electrode assembly extending around the circumference of the distal end portion of the tube, wherein at least the majority of the shaft length is constituted by a twin-walled construction including an inner wall and an outer wall, the tube being hollow, such that a slug of tissue can be pulled through the tube and removed through the proximal end portion of the tube, the twin-walled construction further including an insulating gap between the inner wall and an outer wall to prevent heat from the slug of tissue being transferred from the inner wall to the outer wall of the tube.

2. The device according to claim 1, wherein the twin-walled construction extends substantially to the distal end portion of the tube.

3. The device according to claim 1, wherein the twin-walled construction extends along the tube from the proximal end portion to the distal end portion.

4. The device according to claim 1, wherein the twin-walled construction abuts the second electrode.

5. The device according to claim 4, further comprising a heat-sink member in contact with both the second electrode and the distal end portion of the twin-walled construction.

6. The device according to claim 1, wherein one or both of the walls of the twin-walled construction are formed from a polymer material.

7. The device according to claim 1, wherein the thickness of the walls of the twin-walled construction is less than 0.5 mm.

8. The device according to claim 7, wherein the thickness of the walls of the twin-walled construction is substantially 0.2 mm.

9. The device according to claim 1, wherein the twin-walled construction comprises first and second walls with the gap therebetween containing air.

10. The device according to claim 1, wherein the gap between the walls of the twin-walled construction is less than 1 mm.

11. The device according to claim 1, wherein the gap between the walls of the twin-walled construction is less than 0.5 mm.

12. The device according to claim 1, wherein at least one of the walls of the twin-walled construction includes an entrance to allow material to enter the gap between the walls, and an exit at a different axial position along the shaft to allow material to exit the gap between the walls.

13. The device according to claim 12, wherein the entrance is located at the distal end portion of the tube, and the exit is located at the proximal end portion of the tube, such that the gap between the walls is capable of being used for the extraction of smoke.

14. The device according to claim 13, wherein the entrance is constituted by at least one aperture provided in the at least one wall.

15. The device according to claim 14, wherein said at least one aperture is provided with a shield capable of allowing smoke to be drawn into the twin-walled construction but preventing pieces of tissue from being drawn therein.

16. The device according to claim 15, wherein the shield comprises a mesh extending over said at least one aperture.

17. The device according to claim 15, wherein the shield comprises an outwardly-projecting flange or lip adjacent to said at least one aperture.

18. The device according to claim 12, wherein the entrance is located at the proximal end portion of the tube, and the exit is located at the distal end portion of the tube, such that the gap between the walls is capable of being used for the supply of insufflation fluid.

19. The device according to claim 12, wherein the gap between the walls is provided with dividing means, such that it constitutes at least two passages, a first passage having an entrance located at the distal end portion of the tube, and an exit located at the proximal end portion of the tube, such that the first passage is capable of being used for the extraction of smoke, and a second passage having an entrance located at the proximal end portion of the tube, and an exit located at the distal end portion of the tube, such that the second passage is capable of being used for the supply of insufflation fluid.

20. The device according to claim 19, wherein the dividing means comprises one or more internal walls dividing the gap into the first and second passages.

21. The device according to claim 1, wherein the twin walled construction constitutes a closed system, and there is a vacuum between the walls of the twin-walled construction.

22. The device according to claim 1, wherein there is an inert gas between the walls of the twin-walled construction.

23. The device according to claim 1 wherein there is a solid material between the walls of the twin-walled construction.

24. The device according to claim 1, further comprising a tissue-pulling device locatable within the tube, and capable of pulling tissue against the distal end portion of the tube.

* * * * *